US010682148B2

(12) United States Patent
Huet et al.

(10) Patent No.: US 10,682,148 B2
(45) Date of Patent: Jun. 16, 2020

(54) SYSTEM FOR PARTIALLY CUTTING A BONE

(71) Applicant: OSTESYS, Plouzane (FR)

(72) Inventors: Pierre-Yves Huet, Locmaria-Plouzane (FR); Guillaume Dardenne, Montreuil le Gast (FR); Stephane Lavallee, St Martin d'uriage (FR); Eric Stindel, Locmaria-Plouzane (FR); Christian Lefevre, Brest (FR)

(73) Assignee: OSTESYS, Plouzane (FR)

( * ) Notice: Subject to any disclaimer, the term of this patent is extended or adjusted under 35 U.S.C. 154(b) by 650 days.

(21) Appl. No.: 14/650,032

(22) PCT Filed: Dec. 10, 2013

(86) PCT No.: PCT/EP2013/076139
§ 371 (c)(1),
(2) Date: Jun. 5, 2015

(87) PCT Pub. No.: WO2014/090831
PCT Pub. Date: Jun. 19, 2014

(65) Prior Publication Data
US 2015/0313609 A1    Nov. 5, 2015

(30) Foreign Application Priority Data

Dec. 11, 2012 (FR) ...................................... 12 61877

(51) Int. Cl.
*A61B 17/15*    (2006.01)
*A61B 34/20*    (2016.01)
(Continued)

(52) U.S. Cl.
CPC .......... *A61B 17/151* (2013.01); *A61B 17/152* (2013.01); *A61B 34/20* (2016.02);
(Continued)

(58) Field of Classification Search
CPC combination set(s) only.
See application file for complete search history.

(56) References Cited

U.S. PATENT DOCUMENTS

| 5,147,364 | A |   | 9/1992 | Comparetto |
| 5,275,603 | A | * | 1/1994 | Ferrante ............... A61B 17/157 |
|           |   |   |        | 606/86 R |

(Continued)

FOREIGN PATENT DOCUMENTS

WO    2008005271 A2    1/2008

OTHER PUBLICATIONS

International Search Report from corresponding PCT/EP2013/076139, dated Feb. 10, 2014.
(Continued)

*Primary Examiner* — Jan Christopher L Merene
(74) *Attorney, Agent, or Firm* — Womble Bond Dickinson (US) LLP (57) ABSTRACT

The invention concerns a system for partially cutting a bone, comprising a device for guiding a cutting tool. According to the invention, the device comprises: —an upper face forming a mechanical stop for a first part of the cutting tool, the upper face being non-cutting and thicker than the blade, so as to limit the insertion of the blade into said bone in order to partially cut said bone, the upper stop face having a profile that is a homothety of the edge profile of said hinge, the guide device having a pre-defined range to ensure the steering of the blade of the cutting tool in a pre-defined direction of partial cutting of the bone, —a second part that fastens to the bone and a first fastening means for fastening the guide device to the second part and —a means for adjusting the orientation of the guide device relative to the second part.

17 Claims, 11 Drawing Sheets

(51) Int. Cl.
  *A61F 2/30* (2006.01)
  *A61F 2/46* (2006.01)
  *A61B 90/00* (2016.01)

(52) U.S. Cl.
  CPC . *A61B 2034/2055* (2016.02); *A61B 2090/034* (2016.02); *A61F 2002/30617* (2013.01); *A61F 2002/4662* (2013.01)

(56) References Cited

U.S. PATENT DOCUMENTS

| | | | |
|---|---|---|---|
| 5,722,978 A | 3/1998 | Jenkins | |
| 5,980,526 A * | 11/1999 | Johnson | A61B 17/152 606/86 R |
| 6,385,475 B1 * | 5/2002 | Cinquin | A61B 5/107 128/920 |
| 6,413,261 B1 * | 7/2002 | Grundei | A61B 17/155 606/87 |
| 6,711,432 B1 * | 3/2004 | Krause | A61B 17/15 128/922 |
| 2004/0068187 A1 * | 4/2004 | Krause | A61B 17/15 600/443 |
| 2004/0106926 A1 * | 6/2004 | Leitner | A61B 17/15 606/87 |
| 2005/0113840 A1 * | 5/2005 | Metzger | A61B 17/155 606/88 |
| 2005/0234332 A1 * | 10/2005 | Murphy | A61B 5/4528 600/426 |
| 2008/0195099 A1 * | 8/2008 | Minas | A61B 17/02 606/70 |
| 2011/0160736 A1 * | 6/2011 | Meridew | A61B 17/15 606/89 |
| 2011/0213376 A1 * | 9/2011 | Maxson | A61B 17/151 606/88 |
| 2013/0053855 A1 * | 2/2013 | Bertram | A61B 17/155 606/89 |

OTHER PUBLICATIONS

French Search Report from corresponding FR 1261877, dated Jul. 17, 2013.

* cited by examiner

SYSTEM FOR PARTIALLY CUTTING A BONE

CROSS REFERENCE TO RELATED APPLICATIONS

This application is a § 371 National Stage Application of PCT/EP2013/076139, filed 10 Dec. 2013, which claims priority to FR 1261877, filed 11 Dec. 2012.

BACKGROUND

Field of the Invention

The invention relates to a system and a method for partially cutting a bone.

Description of Related Art

Arthritis is a mechanical anomaly involving a decay of the joints, including the articular cartilage and the sub-chondral bone.

This pathology can be treated through different methods, the most important being the total replacement of the pathological joint by a prosthetic implant. This method is, however, very invasive and sometimes traumatizing for the patient.

When this illness is the result of a misalignment of a member, it can be slowed down or treated by osteotomy.

This less invasive surgical procedure has the purpose of re-balancing the forces exerted on the pathological joint by realigning the joint centers of the member (for example the hip, knee, ankle for the lower member). A partial cut is made on one of the two bones forming the member (for example the femur or the tibia for the lower member).

The realignment is accomplished by causing rotation of the two bone segments, partially cut, about a point of rotation, often called a hinge, resulting from this partial cutting. Once alignment is obtained, these two bone segments are, in most cases, held in the desired position thanks to a bone-forming plate positioned over the cut and attached to both segments.

However, despite the good results of this surgery, the step consisting of accomplishing the partial cut of the bone for obtaining this hinge is particularly difficult to execute and can sometimes lead to failures if it is not accomplished correctly.

This hinge must be correctly dimensioned. If the hinge is too large, the diversion will be very difficult, or even impossible. In the contrary case, if the hinge is too small, it could break during the diversion causing a dissociation of the two bone segments. In this case, the surgical procedure becomes much larger and more complicated because the hinge must be repaired before accomplishing bone-forming.

The great difficulty for the surgeon is thus to know at what time the depth of the cut is sufficient in order to obtain a good size of the hinge. There is in fact no visual reference or any visibility in the conventional incision allowing the surgeon to control the insertion of the saw blade and therefore to manage this cutting depth.

In conventional surgery, the surgeon then inserts, in a first phase, one or two pins depending on the position and the orientation of the desired cut. Fluoroscopic images are acquired through a brightness amplifier to verify the positions and orientations of these pins with respect to the bone. If these positions and orientations are correct, the cut is then effected along these pins. In the contrary case, the procedure is repeated. These fluoroscopic images are a true problem because each acquisition exposes the patient, but also the medical team, to a considerable dose of radiation. Moreover, the orientation of the cut is certainly controlled by the pins, but there is no control over the depth of this cut along these pins and thus on the size of the resulting hinge. There too, the surgeon needs to accomplish several fluoroscopic images with the saw blade inside the bone to check the feeding of this blade with respect to the bone so as to visualize the size of the resulting hinge.

The system called IBALANCE and marketed by the firm ARTHREX supplies a technique allowing the surgeon to control the depth, the position and the orientation of the cut for opening osteotomies. This solution is based on:

A large pin which is inserted outside the conventional incision through the lateral part of the tibia following an axis perpendicular to the frontal plane. The end of the saw blade then enters into collision with this pin when the bone is sufficiently cut, which avoids the destruction of the hinge. This large pin then acts as a mechanical stop for this end of the saw blade.

A guide for the saw blade including a slot which constrains the orientation of this blade so that it is able to cut the bone in the direction of this pin.

Despite the considerable reduction of the fluoroscopic images, the IBALANCE solution has, however, a major disadvantage: it is much more invasive that conventional osteotomies because a large pin is required to be inserted through the knee and outside the conventional incision, which can be very traumatizing for the patient and a source of postoperative complications.

Other solutions based on computer-assisted surgery have been developed these last few decades so as to guide the cut with respect to the bone of the patient. These systems are used during the intervention and most of them consist of a 3D optical localizer which follows and detects specific markers in space. A computer, connected to the localizer, can then automatically calculate the position and the 3D orientation of targets which are composed of at least three of these markers. These targets are then attached, either on surgical tools or on bones so as to obtain their 3D positions and orientations in the surgical volume thanks to this system. In certain solutions used for superior osteotomies of the tibia, the saw blade used for cutting the bone can be localized in 3D with this system. The surgeon can then obtain in real time, through surgical software assisted by the computer, the 3D position and orientation of the saw blade with respect to the bone of the patient during cutting.

This allows the medical team to considerably reduce the doses of radiation required because the control of the cut is entirely accomplished through the computer-assisted surgical system and not be fluoroscopic data.

There are, however, two major problems linked to this solution:

To locate a saw blade, a target is attached to the support of that blade (very often including the motor). The position of the blade with respect to this target is then known by the navigation station (when integrating the 3D data of the support, for example, by calibration). The shape of such a support can vary considerably from one manufacturer to another. The attachment of the target, no matter who the manufacturer is, can then become a real problem. Certain solutions exist for specific supports but these solutions are extremely dependent on the manufacturers.

This solution is not simple to use for the surgeon because it is totally hands free. There is no mechanical constraint which can hold the movement of the surgeon during the cutting procedure and thus avoid possible errors of inattention which can sometimes cause real clinical problems (a cut which finally is to deep or even poorly oriented through lack of attention). The surgeon must take particular care during the osteotomy so as to maintain the desired cutting orientation and to maintain a good size of the hinge. He must consequently check constantly the software during cutting so as to know exactly the position of his saw blade with respect to the bone, while his attention, however, must also bear on his surgical motion. To avoid this, certain surgical instruments localized by the computer-assisted surgical system allow the surgeon to adjust the orientation of the desired cut, through a suitable software interface, and to constrain the orientation of the saw blade, according to this adjustment, through a cutting guide. This solution makes it possible to constrain the orientation of the cut, but there is no instrument allowing adjustment of the depth of the desired cut by limiting the insertion of the saw blade into the bone, and thus avoid too deep a cut.

Documents U.S. Pat. No. 5,722,978 and US 2011/213376 constitute additional prior art.

SUMMARY

The present invention has as its object to supply a system allowing the surgeon to check, in minimally invasive fashion, the depth of the cut for an osteotomy.

A first object of the invention is a system for partially cutting a bone (12), with a view to obtaining two segments of said bone connected together by a bone hinge (39) having an edge (15) with a predetermined profile, the system comprising a guiding device (10) of a cutting tool (130) provided with a blade (13), characterized by the fact that the guiding device (10) has an upper face (3, 18) constituting a mechanical stop for a first part (140) of the cutting tool (130), not cutting and thicker than the blade (13), so as to limit the insertion of the blade (13) into said bone (12) so as to accomplish the partial cutting of said bone, the upper face (3, 18) of the stop having a profile which is a homothety of the profile of the edge (15) of said hinge, the guiding device (10) having an extent predetermined so as to ensure the directional guidance of the blade (13) of the cutting tool (130) along a predetermined orientation of the partial cutting of the bone.

DETAILED DESCRIPTION OF A PREFERRED EMBODIMENT

Moreover, the system comprises a second part (6) serving to attach the bone and a first attachment means (34, 35) to attach the guiding device (10) to the second part (6).

Moreover, the system comprises a means (11) for adjusting the orientation of the guiding device (10) with respect to the second part (6).

According to one embodiment of the invention, the first attachment means (34, 35) makes it possible to detach the second part (6) of the guiding device (10).

According to one mode of realization of the invention, the first attachment means (34, 35) is of the locked mortise and tenon type.

According to one embodiment of the invention, the guiding device (10) includes a means (7) of regulating in translation the position of the upper stop face (3) with respect to the third part (2) of the guiding device (10).

According to one embodiment of the invention, the guiding device includes at least one slot (4, 5) which passes through it from side to side and which is capable of accommodating the blade (13) of the cutting tool (130) and to have it pass through it, the slot (4, 5) of the guiding device (10) having an extent predetermined to ensure the directional guidance of the blade (13) of the cutting tool (130) along the predetermined orientation of the partial cutting of the bone.

According to one embodiment of the invention, the guiding device (10) comprises at least two first and second guides (1, 2) respectively comprising at least one first slot (4) and at least one second slot (5) aligned with the first slot (4), and a means (7) for adjusting in translation the first guide (1) with respect to the second guide (2) following a direction (Z) parallel to the slots (4, 5), the first guide (1) having the upper stop face (3).

According to one embodiment of the invention, the guiding device (10) comprises at least two first and second guiding branches (305, 306), which are attached to one another and are spaced apart, the first branch (305) having the upper stop face (3).

According to one embodiment of the invention, the system includes a set of several stop faces (3, 18) having different shapes of the upper face (18) and/or different heights (17) with respect to the bone, each being capable of serving as a mechanical stop (3, 18) on the guiding device (10).

According to one embodiment of the invention, the system comprises a soft tissue protector (35).

According to one embodiment of the invention, the system comprises a measuring tool with at least one graduation (22) visible by means of intraoperative imagery allowing the user to determine the size of the said hinge depending on the length of the blade (13) of the cutting tool (130).

According to one embodiment of the invention, the system includes an aiming device (21) oriented according to said guiding device, allowing the user to guide the orientation of said system on the bone with respect to a predetermined target point (20) representing the desired hinge.

According to one embodiment of the invention, the system comprises:
- a first target (27) adapted to be attached to said bone,
- a second target (29) adapted to be attached to said upper stop face (3, 18) of the guiding device (10),
- a navigation device (23) which allows acquisition of the three-dimensional positions and orientations of the two targets,
- a processing device (28) which makes it possible to calculate, from the data acquired by said navigation device, said three-dimensional positions and orientations of said upper stop face (3, 18) of the guiding device (10) with respect to said target point, the size of the hinge and said edge of the hinge,
- a display unit (42) which makes it possible to display the information supplied by said processing device (28) to the surgeon.

According to one embodiment of the invention, the system comprises a visual sensor (37) which makes it possible to acquire and to record the three-dimensional position of said target point (41) compared to the first target (27).

According to one embodiment of the invention, the treatment device (28) knows the geometries and positions of the upper face (3, 18) and of said guiding device (10, 4, 5) with respect to the second target (29).

According to one embodiment of the invention, the first target (27) of said bone (12) is attached to a base (31) which is designed to be attached by at least one pin or screw to said bone.

According to one embodiment of the invention, the processing device is designed to calculate the profile of the mechanical stop face (3, 18) to be used according to the size of the desired hinge and the profile of the edge of the desired hinge.

According to one embodiment of the invention, said processing device includes a means which allows modification and updating of the specific length of the blade (13) used for calculating said edge and of said size of the hinge.

According to one embodiment of the invention, said display unit (42) and/or said processing device (28) is directly carried by at least one of said targets (27, 29).

A second object of the invention is a method for partially cutting a bone (12) with a view to obtaining two segments of said bone (12) connected together by a bone hinge (39) having an edge (15) with a predetermined profile, using the system as described above, said method including the following steps:
- identification of a target point (41) on said bone representing the desired target hinge (39),
- adjusting the position of the upper face (3, 18) of the guiding device (10) according to the size of the desired hinge (39) and the length of the blade (13) of the cutting tool (130),
- visualization of the edge (15) and of the size of the bone hinge (39),
- cutting said bone by displacement of said cutting tool (130) in the guiding device (10) (or in the slot (4, 5) of this guiding device (10)), until said non-cutting part (140) of said cutting tool (130) touches said upper face (3, 18) and along said upper face (3, 18) of the guiding device (10).

According to one embodiment of the invention, said upper mechanical stop face (3, 18) of the guiding device (10) is adjusted toward said target point.

According to one embodiment of the invention, said size of the hinge (39) is the distance between said target point (20) and said edge of the hinge (15).

According to one embodiment of the invention, said orientation of the guiding device (10) with respect to said target point (20) is visualized by using at least the intraoperative imagery means.

According one embodiment of the invention, said edge (15) of the hinge and said size (39) of the hinge are visualized by using at least the interaoperative imagery means.

According to one embodiment of the invention, said orientation of the guiding device (10) with respect to said target point (41) is visualized by using at least one navigation station.

According to one embodiment of the invention, said edge (15) of the hinge and said size (39) of the hinge are visualized by using at least one navigation station.

The invention and its advantages are described in more detail hereafter with reference to the appended schematic drawings which, solely for the purpose of illustration, show certain non-limiting embodiments, drawings wherein.

The detailed description hereafter makes reference principally to the opening osteotomy of the tibia. The present invention can however also be used with other types of osteotomy.

Figure 1:
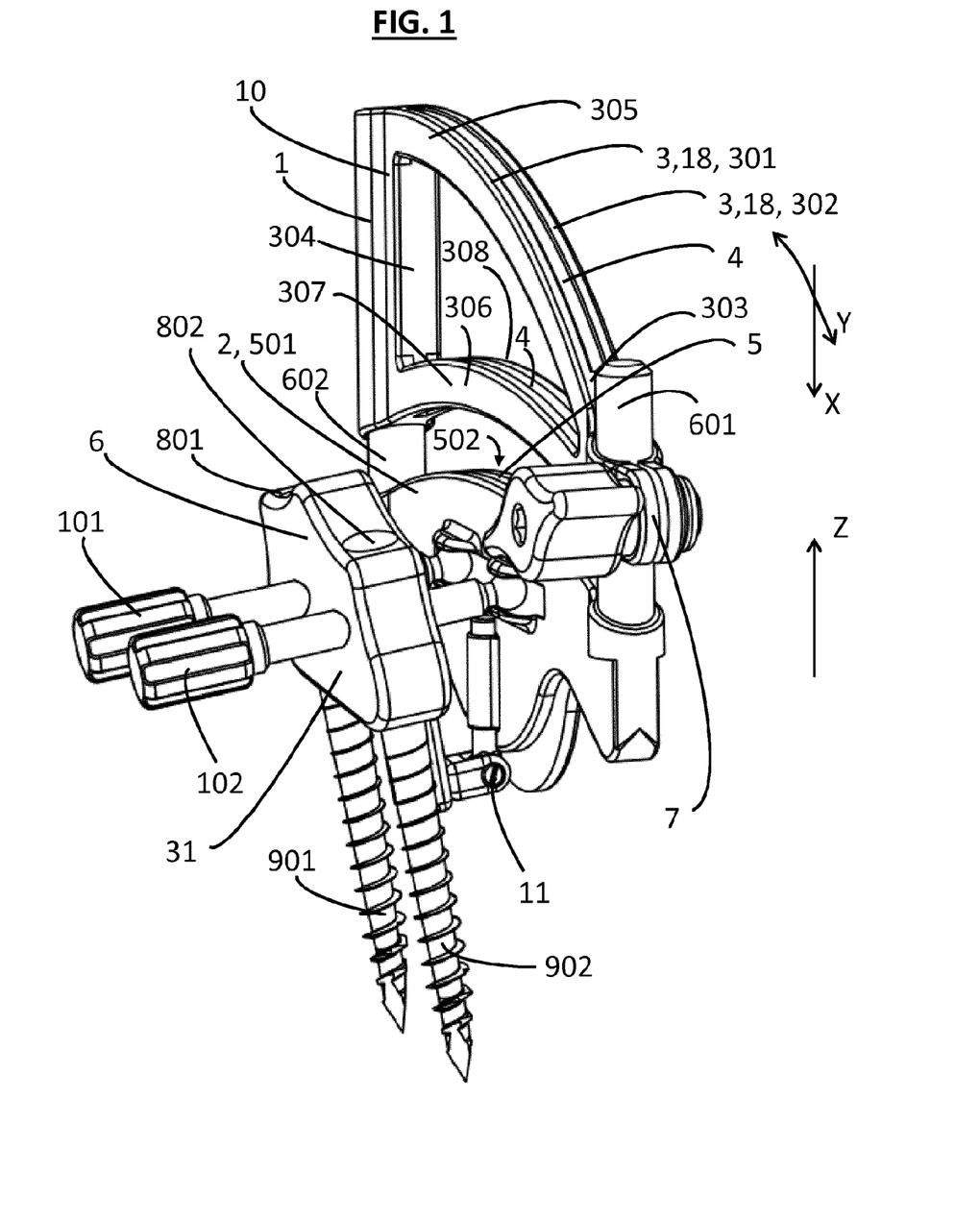
FIG. 1 is a schematic representation of a possible mode of accomplishment of a mechanical stop system which is a part of the system according to the present invention.

In one embodiment, FIG. 1 shows the system according to the invention, having a mechanical stop 3 and including:

A guiding device (10) (also called hereafter the first part (10)) provided for guiding the displacement of the cutting tool (130) in a predetermined orientation. For example, according to one embodiment, this guiding device (10) is capable of accommodating the cutting tool (130) and to have it pass through it. The guiding device (10) can comprise for example an upper guide (1) and a lower guide (2) oriented along the direction of the desired cut (predetermined orientation). The guiding device (10), for example its upper guide (1), has at least one upper face (3) which is a homothety of the shape of the resulting hinge and which forms a stop (3) for a cutting object (130) which will be explained hereafter (where this face (3) is called the stop face (3) or mechanical stop system (3)). The guiding device (10), to wit for example the upper guide (1), has a guiding means, to wit for example a slot (4), allowing the blade (13) of the cutting object (130) to be suitably oriented along the mechanical stop system. The first slot (4) is for example formed between the two first and second parts (301) and (302) which are face-to-face following the direction of the thickness of the slot (4). The stop face (3) is for example provided on the upper side of the first and second parts (301) and (302) delimiting the thickness of the slot (4). For example, the lower guide (2) thus possesses a guiding means, to wit for example another slot (5). The second slot (5) is for example formed between the two parts (501) and (502) of the guide (2). The slots (4, 5) are aligned. The slots(s) (4, 5) extend in one and the same plane formed by the direction X of insertion of the blade (13) into the bone and the profile Y of displacement of the cutting tool (130) along the stop face (3). Generally, the guiding device (10) provides by said guiding means (for example the slot(s) (4, 5)) and/or by guiding means other than slots, directional guidance of the blade (13) of the cutting tool (130) according to a predetermined angular orientation, which is the plane formed by the direction X of insertion of the blade (13) into the bone and by the profile (Y) of displacement of the cutting tool (130) along the stop face (3). This plane, formed by X and Y, wherein the blade (13) is mobile, is limited along the profile Y (called the longitudinal direction Y) by a first end (303) of the guide (1) and/or of the guide (2), and by a second distinct end (304) of the guide (1) and/or of the guide (2). The slot(s) (4, 5) extend between the two ends (303) and (304). The two ends (303) and (304) serving as stops for the blade (13). Any other means of guiding the cutting object can also be used within the scope of this invention. At least one guiding means is necessary. According to one embodiment of the invention, the upper face (3, 18) is adjustable in translation in height with respect to the bone and/or along the cut. For example, the direction of this translation is parallel to the slots (4, 5). For example a means of adjusting the upper guide (1) in translation or depth in the direction Z being included in the plane of X and Y with respect to the lower guide (2) can be provided, for example thanks to two rails (601) and (602), a tightening system (7) can be provided to allow this translation to be attached once the adjustment is correctly carried out. Any other means of adjustment for the translation of the upper guide (1) with respect to the lower guide (2) can be used in the framework of this invention. In the first guide (1), the slot (4) can be delimited by several branches, to wit a first upper branch (305) bearing the upper stop face (3), and a lower branch (306) cohesive with the first upper branch (305) and also delimiting the slot (4), the branch (306) having two facing parts (307) and (308) face to face delimiting the thickness of the slot (4).

A second part (6) serving to attach the guiding device (10) and of the system with respect to the bone, this second part (6) having for example two holes (801) and (802) which can respectively accommodate two pins (901) and (902) for attachment to the bone. There too, any other means of attachment of the guiding device (10) and of the system with respect to the bone can be used within the scope of this invention.

According to one embodiment, the first part (10) is adjustable in orientation with respect to the second part (6), and consequently with respect to the bone, for example through two adjusting wheels (101) and (102) about the joint (11). Two rotations can be adjusted with these wheels: about the longitudinal axis Y and about the lateral axis Z of the mechanical stop system, but the third rotation about the vertical axis perpendicular to the axes Y and Z could also be adjusted within the scope of this invention. There too, any other means of adjustment for orientation of the mechanical stop system with respect to the bone can be used within the scope of this invention.

Figure 2:
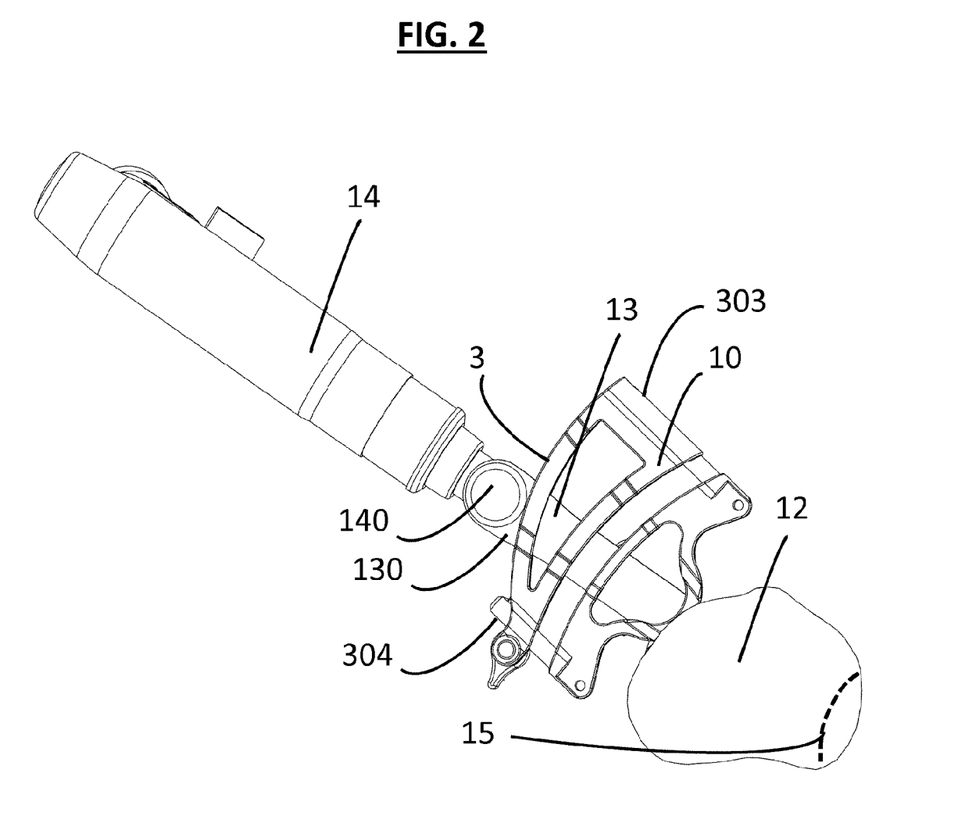
FIG. 2 is a schematic representation of the cutting of the bone with the cutting object along the system of mechanical stops according to FIG. 1.

According to one embodiment, FIG. 2 shows the mechanical stop system attached to the bone (12). The blade (13) of the cutting tool (130) is displaced in the slot(s) (4, 5) or generally with respect to the guiding device (10), by having the orientation determined by the guiding device (10) to accomplish the partial cutting of the bone. The cutting object (130) supported by a motor (14) makes it possible to the surgeon to accomplish the cutting of the bone (12) according to the orientation and the depth of the mechanical stop system (3, 18). The cut is guided through the slot (4) and/or (5) but any other guiding means for the cutting object can be used within the scope of this invention. The cut is then accomplished all along the length of the blade (13) until the part (140) comes into contact with the profile of the mechanical stop system (3), thus stopping the progression of the blade (13) into the bone (12). This procedure is reiterated all along the profile of the mechanical stop system (3). The resulting hinge (39) of the bone has consequently one edge (15) which is the homothety of the profile of the mechanical stop system (3). The profile of the mechanical stop system (3) depends on the shape of the desired hinge (39). Any other profile of the mechanical stop system can also be used within the framework of the invention.

Figure 3:
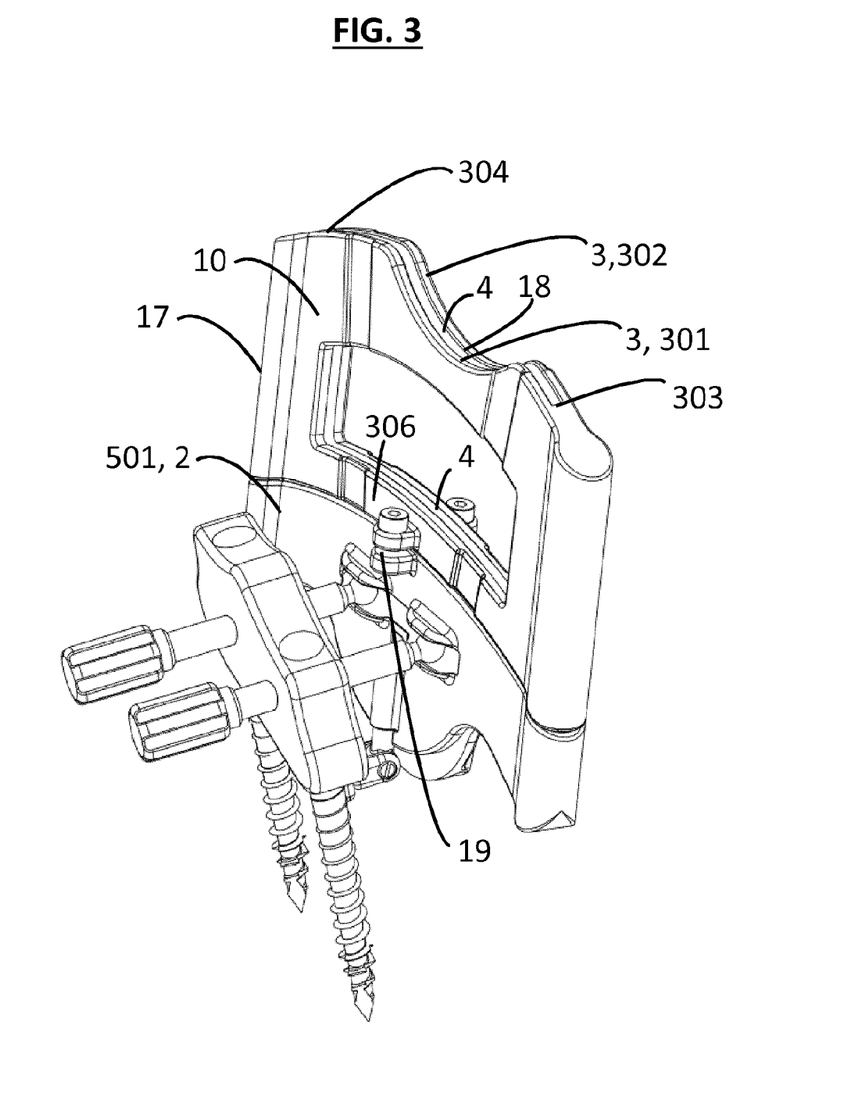
FIG. 3 is a schematic representation of the second version of the mechanical stop system with an upper edge having a different shape and depth.

According to one embodiment, FIG. 3 shows another version of the mechanical stop system (3). In this case, different shapes, types, profiles or dimensions of the guiding device (10) and of its stop face (3) or (18), can have different heights (17) and different shapes and/or different upper stop face (3) profiles are available, being called models hereafter. The model is selected among the set of several models by the surgeon according to the shape and the size of the desired hinge (39). The guiding device (10) selected is then attached to the second lower attachment part (2) through an attachment means (19), which can for example comprise a screw (19). Any other means of attachment can also be used within the scope of this invention.

Figure 4:
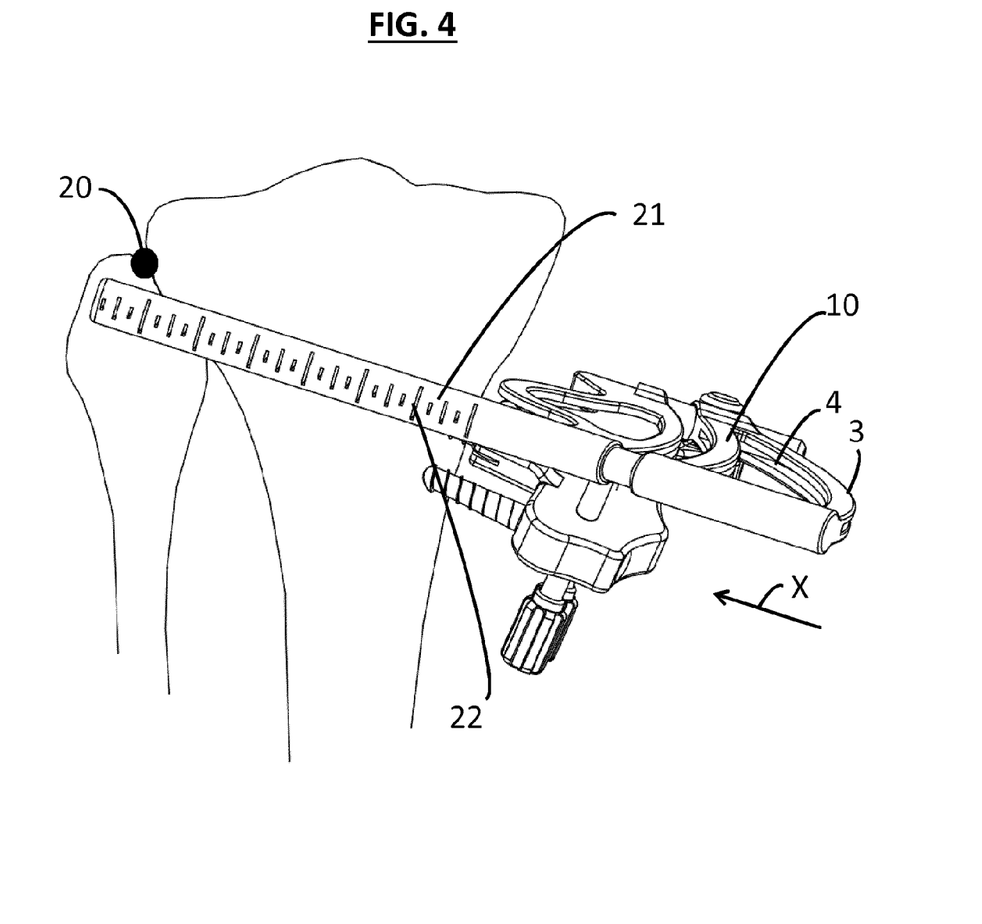
FIG. 4 is a schematic representation of the third version of the mechanical stop system with an aiming system.

According to one embodiment, FIG. 4 shows a means allowing the surgeon to visualize the orientation and the depth of the mechanical stop system (3) with respect to the bone and more precisely with respect to a target point (20) representing the desired hinge (39). The guiding device (10) has an aiming system (21) having for example the shape of a ruler, oriented according to the guiding means of the mechanical stop system (3) and allowing the surgeon with the aid of intraoperative imaging means such as, for example, fluoroscopic images, to adjust the orientation of the mechanical stop system (3) toward the target point. The graduation (22) of the aiming system can also be visible by this intraoperative imaging means. The surgeon then adjusts the depth of the mechanical stop system (3) in the X direction according to the size of the desired hinge, that is the difference between the value of the indicated distance on the graduation corresponding to the target point (20) and the length of the blade (13). Any other imagery means and aiming system allowing the surgeon to adjust and to visualize the position and the orientation of the mechanical stop system can be used within the scope of this invention.

Figure 5:
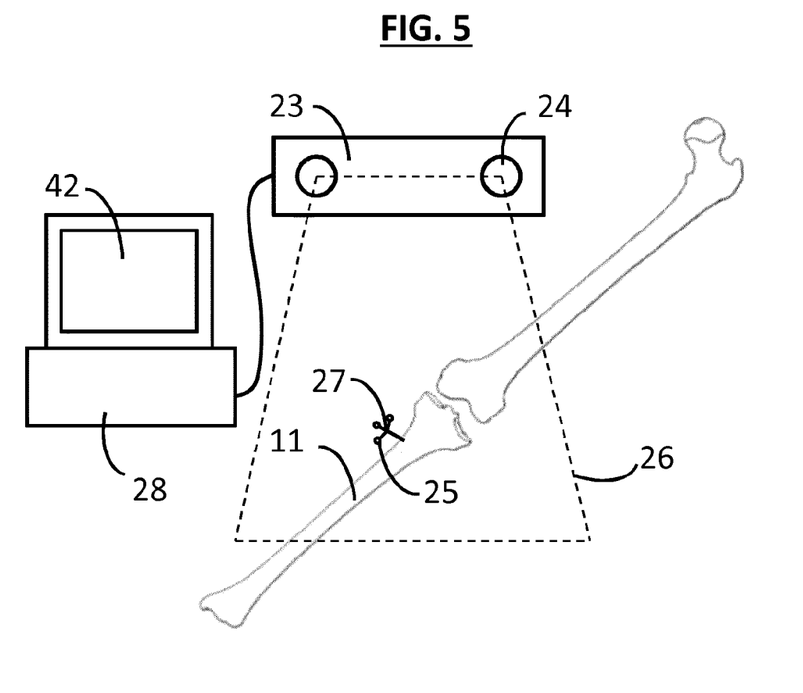
FIG. 5 is a schematic representation of the equipment necessary for using the fourth version of the mechanical stop system.

According to one embodiment, FIG. 5 shows another method allowing a surgeon to visualize and adjust orientation and depth of the mechanical stop system (3). The equipment consists of a 3D localizer (23) equipped with cameras (24) which can determine by triangulation the 3D positions of the markers (25) in space (26) visible by the localizer. A target (27) of known type, containing at least three markers (25) and allowing a processing system (28) connected to the localizer (23) to calculate their 3D positions and orientations, is attached to the bone. The target (27) and the localizer (23) can be any kind of system available on the market, such as for example that marketed by the NORTHERN DIGITAL under the POLARIS brand.

Figure 6:
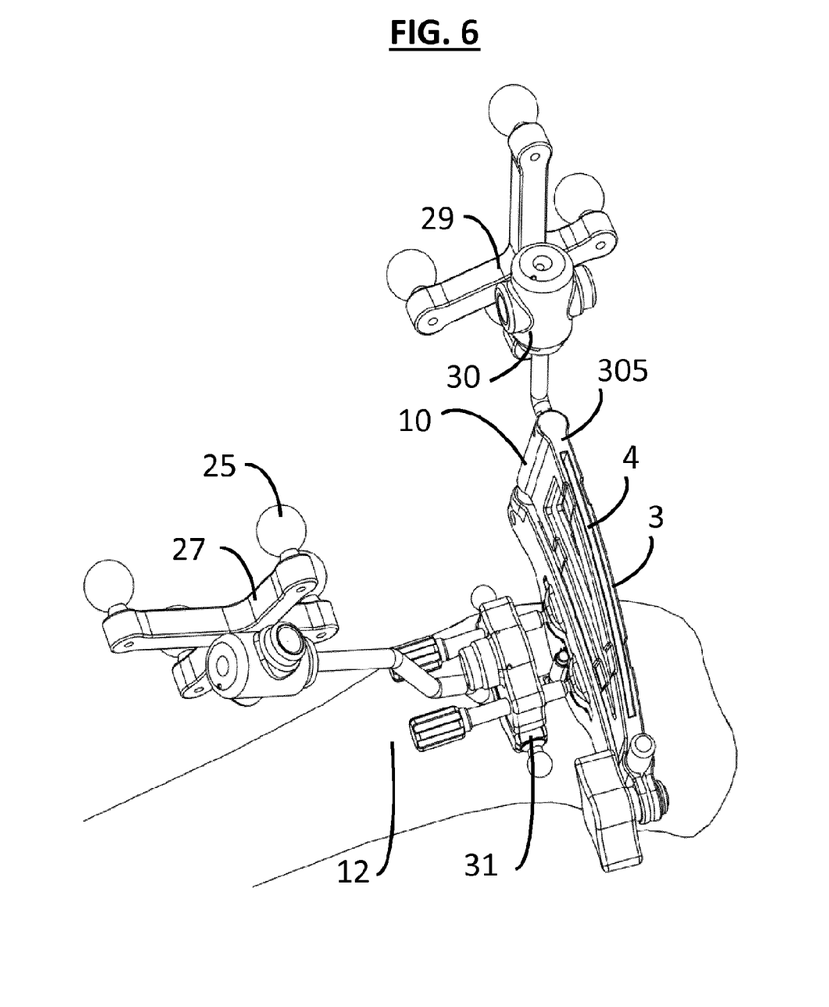
FIG. 6 is a schematic representation of the fourth version of the mechanical stop system attached to the bone.

According to one embodiment, FIG. 6 shows the mechanical stop system (3) attached to the bone (12) by this means. A target (29) is attached to the guiding device (10) (for example on its upper branch (305)), to allow the localizer (23) to obtain the 3D position and the orientation of the device (10). If necessary, this target (29) can be easily withdrawn from the guiding device (10) through an attachment system (30). The target (27) is attached on the bone (12) through a base (31) allowing the localizer (23) to obtain the position and the 3D orientation (3D meaning three-dimensionally) of the bone in the surgical volume. The guiding device (10) and its mechanical stop system (3) can then be directly attached to the bone (12) through the same base (31) (forming in this case the second part (6) indicated above), so as to avoid multiple attachment systems and multiple pins inside the bone. Within the scope of this invention, the target (29) and the mechanical stop system (3) can be attached to the bone by any other means.

Figure 7:
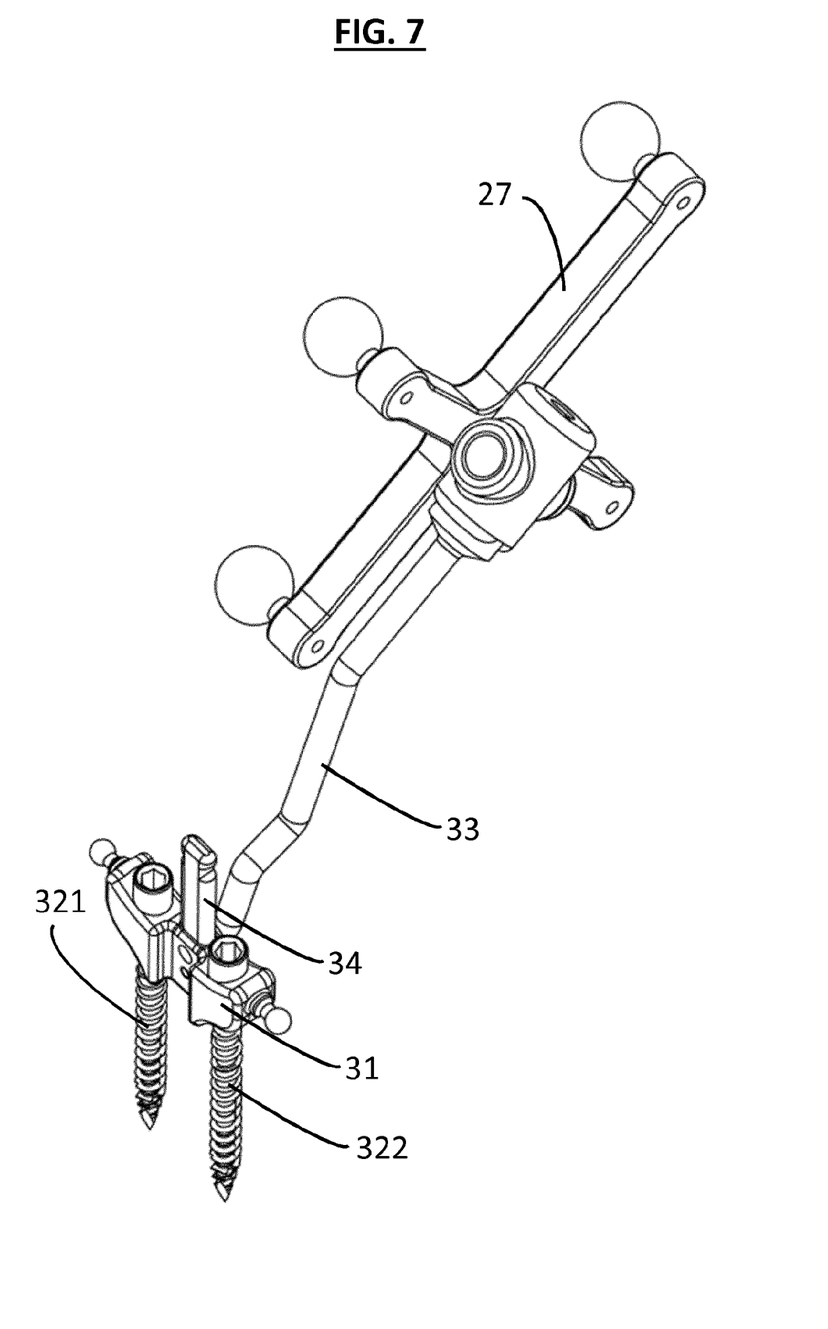
FIG. 7 is a schematic representation of the means of attaching a target to the bone.
Figure 8:
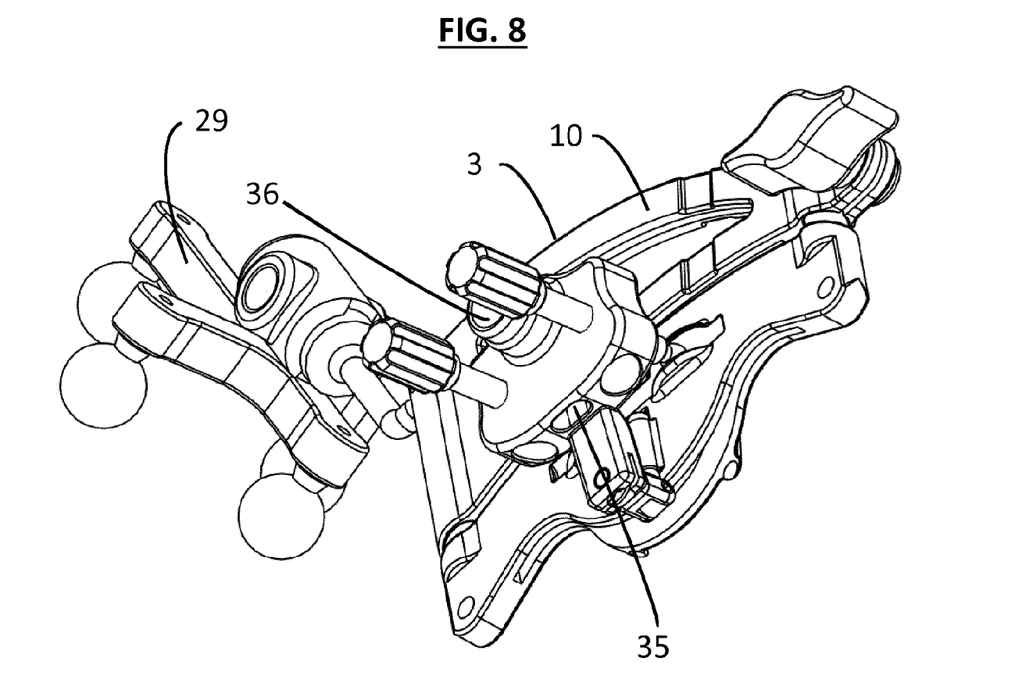
FIG. 8 is a schematic representation of the rear view of the fourth version of the mechanical stop system.

According to one embodiment, FIG. 7 shows a base (31) which can accommodate two pins (321) and (322) so as to attach the base (31) to the bone, and which comprises a target support (33) allowing the base (31) to receive the corresponding target which is, in this case, the target (27). The guiding device (10) and its mechanical stop system (3) can be attached to this base (31) through an attachment system (34, 35): for example a tenon (34) provided on the base (31), which tenon cooperates with a mortise (35) provided on the guiding device (10) as illustrated in FIG. 8. This attachment system (34, 35) can be easily locked with a button (36). In the frame of this invention, the mechanical stop system (3) can be attached to the bone by any other attachment means.

Figure 9:
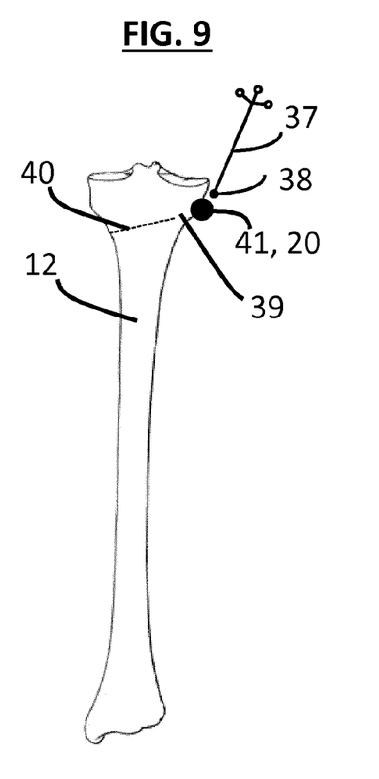
FIG. 9 is a schematic representation of the acquired point representing the target hinge for an osteotomy of the tibia.

According to one embodiment, in FIG. 9, the target point (20, 41) can be obtained with this means using a sensor (37) consisting of markers and of a pointer (38) available on the market with the localization system such as for example that marketed by the NORTHERN DIGITAL company. The surgeon then acquires the target point (20, 41) on the bone with this sensor. The equipment and the processing system records the 3D position of this point with respect to the target (27) attached on the bone. Knowing the position of this target point (20, 41), the position of the mechanical stop system (3) thanks to its target (29) and the length of the blade (13) of the cutting object, the processing system can then calculate:

The orientation and the relative positions of the mechanical stop system (3) relative to the target point (20, 41), The size of the hinge (39), that is the distance between the cut (40) which would be accomplished along the mechanical stop system (3) and the acquired point (20, 41), The information can be supplied to the surgeon in real time during the adjustment of the mechanical stop system (3) by means of specific software, and by a screen (42) that is part of the equipment as illustrated in FIG. 5. If necessary, the software can allow the surgeon to modify the length of the blade (13) and update the information shown.

Figure 10:
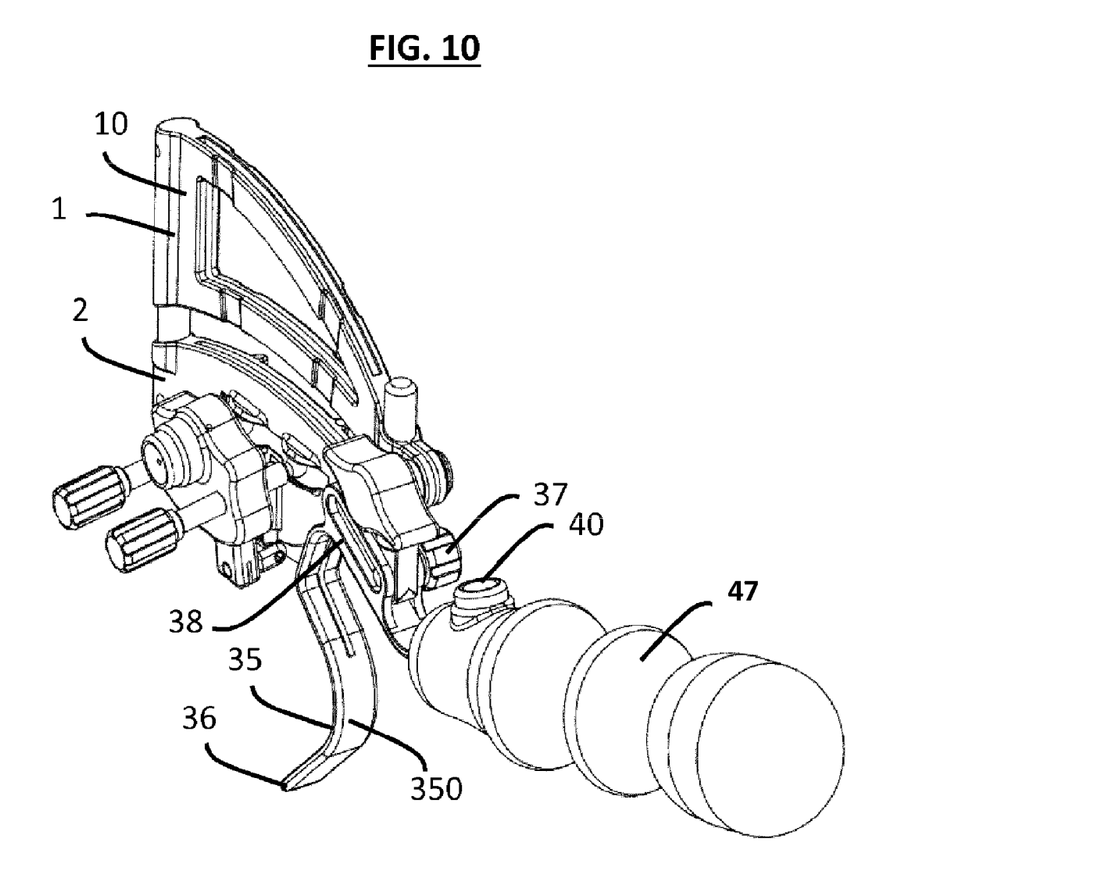
FIG. 10 is a schematic representation of the mechanical stop system with a soft tissue protector.

According to one embodiment, FIG. 10 shows a version of the mechanical stop system (3) with a soft tissue protector (350), including:

Another elongated branch (35) oriented along the same direction as the future cut and which can be inserted, through the incision, between the bone and the soft tissue so as to protect this tissue from the cutting. The end (36) of this elongated branch (35) acts as a spacer during insertion so as to easily lodge the protector (350) between the bone and the tissue. The branch (35) of the protector (350) also has a curved form which adapts perfectly to the shape of a bone so as to reduce the space required for its insertion. Any other form of the protector can also be used under this invention.

An attachment system allowing the protector (350) to be attached to the guiding device (10), for example to its lower guide (2). For example, this attachment system consists of a screw (37) passing through an oblong hole of a tab (38) guiding this screw (37), the screw being tightened into position in the hole, so that the protector (350) will be properly oriented with respect to the cut. Any other method of attachment of the protector can be used within the scope of this invention.

A gripper (47) which allows the user to easily insert the protector between the bone and the soft tissues and which can be removed, if necessary, from the rest of the protector by means of an attachment system locked with a button (40). Any other gripping means can also be used in the scope of this invention.

In an osteotomy of the tibia, several nerves and blood vessels are situated in the posterior portion of the tibia. These tissues must in no case be cut during osteotomy, which could cause considerable clinical damage. This posterior protector can consequently be slid between these soft tissues and the bone through the incision so as to ensure that the cutting object (13) will not cut these nerves and blood vessels. Within the scope of this invention, any other type of protector can also be used.

Figure 11:
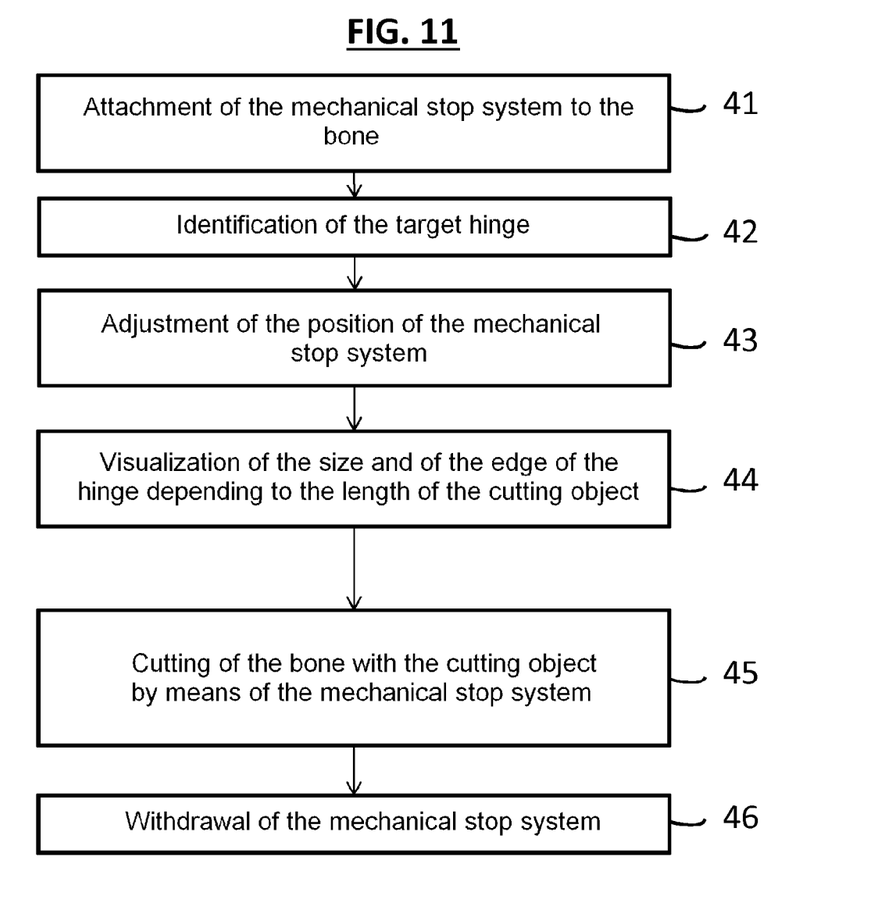
FIG. 11 is the flow diagram of the surgical procedure implemented.

According to one embodiment, FIG. 11 shows all of the surgical procedure having several specific steps for partially cutting a bone. After having attached the mechanical stop system (3) onto the bone (step 41), the position of the target hinge (39) is in a first step identified by the surgeon (step 42). The position of the guiding device (10) and/or of the mechanical stop system (3) is then adjusted to control the depth of the cut (step 43). The surgeon visualizes the size of the hinge (39), that is the distance between the cutting limit and the target hinge, depending on the length of the blade (13) (step 44). Once the mechanical stop system (3) is correctly adjusted, the surgeon accomplishes the cut along the guiding device (10) and along the mechanical stop system (3), until the non-cutting part (140) of the tool (130) touches the upper stop face (3). This procedure is repeated along the profile of the upper stop face (3) (step 45). The shape of the resulting hinge (39) is then the homothety of the profile of the upper stop face (3). The procedure is terminated; the surgeon can then withdraw the system from the bone (step 46).

The principal advantage of this invention is to supply a less invasive system allowing the surgeon to control the depth of cutting for an osteotomy.

The invention claimed is:

1. A system for partially cutting a bone, with a view to obtaining two segments of said bone interconnected by a bone hinge having an edge with a predetermined profile, the system comprising
    a cutting tool comprising a blade and a non-cutting part thicker than the blade;
    a guiding device comprising a slot configured for guiding the cutting tool, wherein the slot extends in a plane defined by a first axis and a second axis from a upper stop face of the guiding device constituting a mechanical stop for the non-cutting part of the cutting tool, so as to limit insertion of the blade into said bone and to carry out partial cutting of said bone to form the hinge, the upper stop face having a non-straight profile which is a homothety of a profile of an edge of said hinge, the slot having an extent predetermined to ensure directional guidance of the blade of the cutting tool in a predetermined orientation of partial cutting of the bone,
    a fixation part configured to be attached to the bone,
    an attachment configured to attach a lower portion of the guiding device opposite to the upper stop face with respect to the slot to the fixation part,
    an orientation mechanism operable for controlling an orientation of the guiding device with respect to the fixation part about the first axis and the second axis,
    a first tracker configured to be attached to the bone,
    a second tracker configured to be attached to the guiding device, a localizer configured to acquire three-dimensional positions and orientations of the first and second trackers, and a processing device configured to calculate, from data acquired by the localizer, a three-dimensional position and orientation of said upper stop face of the guiding device with respect to a target point representing the hinge, the size of the hinge and said edge of the hinge.

2. The system according to claim 1, wherein the guiding device is removable from the fixation part.

3. The system according to claim 1, wherein the attachment mechanism is of a locked mortise and tenon type.

4. The system according to claim 1, wherein said guiding device comprises a means of controlling in translation the position of the upper stop face with respect to a third part of the guiding device.

5. The system according to claim 1, wherein said guiding device comprises at least one slot which passes through said guiding device from side to side and which is capable of accommodating the blade of the cutting tool and to have the blade pass through the guiding device, the slot of the guiding device having an extent predetermined to ensure directional guidance of the blade of the cutting tool according to the predetermined orientation of partial cut of the bone.

6. The system according to claim 5, wherein said guiding device includes at least two first and second guides respectively comprising at least one first slot and at least one second slot aligned with the first slot, and a means for adjusting the first guide in translation with respect to the second guide in a direction (Z) parallel to the slots, the first guide having the upper stop face.

7. The system according to claim 1, wherein said guiding device comprises at least two first and second guiding branches, which are interconnected and which are spaced apart, the first branch having the upper stop face.

8. The system according to claim 1 further comprising a set of several interchangeable stop faces having different forms of upper stop face and/or different heights with respect to bone, each being able to serve as a mechanical stop on the guiding device.

9. The system according to claim 1 further comprising a soft tissue protector.

10. The system according to claim 1 further comprising a measuring tool with at least one graduation visible by means of intraoperatory imagery allowing a user to determine the size of said hinge depending on the length of the blade of the cutting tool.

11. The system according to claim 1 further comprising an aiming device oriented according to said guiding device, allowing a user to guide the orientation of said system on a bone with respect to the target point.

12. The system according to claim 1 further comprising a pointer visible by the localizer which makes it possible to acquire and to record the three-dimensional position of said target point with respect to the first tracker.

13. The system according to claim 1, wherein the first tracker of said bone is attached to a base which is adapted to be attached by at least one pin or screw to said bone.

14. The system according to claim 1, wherein said processing device is configured to modify and update a specific length of the blade used for calculating said edge and said size of the hinge.

15. A system for partially cutting a bone, with a view to obtaining two segments of said bone interconnected by a bone hinge having an edge with a predetermined profile, the system comprising:

a guiding device comprising a slot configured for guiding a cutting tool provided with a blade, wherein the slot extends in a plane defined by a first axis and a second axis from a upper stop face of the guiding device constituting a mechanical stop for a non-cutting part of the cutting tool thicker than the blade, so as to limit insertion of the blade into said bone and to carry out the partial cutting of said bone to form the hinge, the upper stop face having a non-straight profile which is a homothety of the profile of the edge of said hinge, slot having an extent predetermined to ensure directional guidance of the blade of the cutting tool in a predetermined orientation of partial cutting of the bone, a fixation part serving for attachment to the bone;

an attachment mechanism configured to attach a lower portion of the guiding device opposite to the upper stop face with respect to the slot to the fixation part;

an orientable mechanism operable to control the orientation of the guiding device with respect to the fixation part about the first axis and the second axis, a first tracker configured to be attached to said bone, a second tracker configured to be attached to said upper stop face of the guiding device, a localizer configured to acquire the three-dimensional positions and orientations of the first and second trackers, a processing device configured to calculate, based on data acquired by said localizer, said three-dimensional positions and orientations of said upper stop face of the guiding device with respect to target point representing the hinge, the size of the hinge and said edge of the hinge, to calculate a profile of the mechanical stop face to be used depending on the size of a desired hinge and the profile of the edge of the desired hinge, a display unit configured to display information supplied by said processing device to a surgeon.

16. The system according to claim 15, wherein said processing device is configured to modify and update the specific length of the blade used for calculating said edge and said size of the hinge.

17. A method for partially cutting a bone with a view to obtaining two segments of this bone interconnected by a bone hinge having an edge of predetermined profile, using the system of claim 1, said method comprising:

acquiring three-dimensional positions and orientations of the first and second trackers by the localizer, identifying a target point on said bone representing the hinge, computing, by the processing device, a position and an orientation of the upper stop face of the guiding device according to the size of the target hinge and the length of the blade of the cutting tool, adjusting the position and orientation of the upper stop face of the guiding device based on the computed position and orientation, cutting said bone by displacement of said cutting tool in the guiding device or in a slot of said guiding device, until said non-cutting part of said cutting tool reaches said upper stop face and along the upper stop face of the guiding device.

* * * * *